United States Patent
Yoon

(10) Patent No.: US 11,353,218 B2
(45) Date of Patent: Jun. 7, 2022

(54) INTEGRATED MANAGEMENT METHOD AND SYSTEM FOR KITCHEN ENVIRONMENT USING ARTIFICIAL INTELLIGENCE

(71) Applicant: LG ELECTRONICS INC., Seoul (KR)

(72) Inventor: Yoosool Yoon, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 17/075,464

(22) Filed: Oct. 20, 2020

(65) Prior Publication Data

US 2021/0164663 A1 Jun. 3, 2021

(30) Foreign Application Priority Data

Nov. 29, 2019 (KR) ................. 10-2019-0157411

(51) Int. Cl.
| | |
|---|---|
| *F24C 15/20* | (2006.01) |
| *G01N 33/00* | (2006.01) |
| *H04L 12/28* | (2006.01) |
| *H04W 4/38* | (2018.01) |
| *G06N 3/08* | (2006.01) |
| *H04L 67/125* | (2022.01) |

(52) U.S. Cl.
CPC ..... *F24C 15/2021* (2013.01); *G01N 33/0063* (2013.01); *G06N 3/08* (2013.01); *H04L 12/2816* (2013.01); *H04L 67/125* (2013.01); *H04W 4/38* (2018.02); *H04L 2012/285* (2013.01); *H04L 2012/2841* (2013.01)

(58) Field of Classification Search
CPC . F24C 15/2021; F24C 15/20; G01N 33/0063; G06N 3/08; G06N 5/003; G06N 7/005; G06N 20/10; G06N 20/20; G06N 20/00; H04L 12/2816; H04L 67/125; H04L 2012/2841; H04L 2012/285; H04L 12/2825; H04L 12/2829; H04W 4/38; A47L 15/0021; A47L 2401/04; A47L 2501/07; A47L 2501/26; A47L 2501/30; A47L 15/0063; Y02D 30/70; G06Q 50/10; F24F 11/63; G06K 9/62; G08B 21/182; H04N 7/18
See application file for complete search history.

(56) References Cited

U.S. PATENT DOCUMENTS

2017/0108236 A1* 4/2017 Guan .................. H05B 47/105

* cited by examiner

*Primary Examiner* — Tejal Gami
(74) *Attorney, Agent, or Firm* — Lee Hong Degerman Kang & Waimey

(57) ABSTRACT

Disclosed are an integrated management method and system for a kitchen environment using artificial intelligence. The integrated management system for the kitchen environment includes: a range hood placed above a cooking appliance including a heater, the range hood including a sensor that measures information on an atmosphere environment changed due to an operation of the cooking appliance; a server determining whether to execute a kitchen environment management mode, on the basis of a result of measurement by the sensor; and multiple environment appliances registered in a user account and cooperating over a network, each of the multiple environment appliance receiving a control command corresponding to the kitchen environment management mode from the server, and operating according to the control command.

15 Claims, 9 Drawing Sheets

INTEGRATED MANAGEMENT METHOD AND SYSTEM FOR KITCHEN ENVIRONMENT USING ARTIFICIAL INTELLIGENCE

CROSS REFERENCE TO RELATED APPLICATION

Pursuant to 35 U.S.C. § 119(a), this application claims the benefit of earlier filing date and right of priority to Korean Patent Application No. 10-2019-0157411, filed Nov. 29, 2019, the contents of which are all hereby incorporated by reference herein in its entirety.

BACKGROUND OF THE INVENTION

Field of the Invention

The present disclosure relates to an integrated management method and system for a kitchen environment using artificial intelligence. More particularly, the present disclosure relates to a method and a system for integrally controlling an environment appliance by using artificial intelligence, on the basis of an atmosphere environment in a kitchen which is changed due to an operation of a cooking appliance.

Description of the Related Art

As technology has advanced, devices equipped with artificial intelligence (AI) have been widely introduced. In particular, home appliances to which Internet of Things (IoT) technology is applied so as to be connected to a network are also implemented in such a manner as to have artificial intelligence.

In an IoT environment, an intelligent Internet Technology (IT) service that collects and analyzes data generated by connected devices to create new value in human life may be provided. Through convergence and combination of existing IT and various industries, IoT may be applied to fields such as smart homes, smart buildings, smart cities, smart cars, smart appliances, and the like.

In the meantime, environment appliances equipped with artificial intelligence may be installed in the home kitchen for use convenience. For example, a range hood, a cooking appliance, and an environment appliances connected over a network may operate in conjunction with each other for effective processing of pollutants generated during cooking.

The foregoing is intended merely to aid in the understanding of the background of the present disclosure, and is not intended to mean that the present disclosure falls within the purview of the related art that is already known to those skilled in the art.

SUMMARY OF THE INVENTION

The present disclosure provides an integrated management method of a kitchen environment using artificial intelligence.

In addition, the present disclosure provides an integrated management system for a kitchen environment using artificial intelligence.

It is to be understood that technical problems to be solved by the present disclosure are not limited to the aforementioned technical problems and other technical problems which are not mentioned will be apparent from the following description to those skilled in the art.

According to several embodiments of the present disclosure, there is provided an integrated management system for a kitchen environment using artificial intelligence, the system including: a range hood placed above a cooking appliance including a heater, the range hood including a sensor that measures information on an atmosphere environment changed due to an operation of the cooking appliance; a server determining whether to execute a kitchen environment management mode, on the basis of a result of measurement by the sensor; and multiple environment appliances registered in a user account and cooperating over a network, each of the multiple environment appliance receiving a control command corresponding to the kitchen environment management mode from the server, and operating according to the control command.

In various embodiments of the present disclosure, the sensor may detect at least one among gas, oil mist, and smoke discharged due to the operation of the cooking appliance.

In various embodiments of the present disclosure, the range hood may transmit a warning signal to the server when the at least one among the gas, the oil mist, and the smoke detected by the sensor is equal to or greater than a predetermined threshold value, and the server may control the cooking appliance so that output of the cooking appliance is decreased, when the warning signal is provided.

In various embodiments of the present disclosure, the system may further include a user terminal displaying details of the control commands provided to the multiple environment appliances, wherein the server may provide the user terminal with a warning message in a warning mode, and the user terminal may output the warning message.

In various embodiments of the present disclosure, the range hood may further include a camera photographing the cooking appliance, and the range hood may transmit an image of the cooking appliance photographed by the camera to the server.

In various embodiments of the present disclosure, the server may detect a change in the information on the atmosphere environment by using a learning model in which the image of the cooking appliance and the information on the atmosphere environment are previously stored.

In various embodiments of the present disclosure, the camera placed above the cooking appliance may acquire an image of cookware with which cooking is performed, and the server may estimate a degree of pollution of the cookware by using a pollution degree model of the cookware in which the image of the cookware and a variation of the atmosphere environment are previously stored.

In various embodiments of the present disclosure, the multiple environment appliances may include a dishwasher, and the server may determine a washing cycle of the dishwasher, washing time, and an amount of detergent on the basis of the estimated degree of pollution.

In various embodiments of the present disclosure, the multiple environment appliances may include an air purifier or an air conditioner, and the server may generate, when the kitchen environment management mode is executed, the control command for increasing output of the air purifier or the air conditioner, and may provide the control command to the environment appliance.

According to several embodiments of the present disclosure, there is provided an integrated management method of a kitchen environment using artificial intelligence, the method including: measuring, by a range hood placed above a cooking appliance including a heater, information on an atmosphere environment changed due to an operation of the cooking appliance, by using a sensor; determining, by a server on the basis of a result of measurement, whether to execute a kitchen environment management mode; driving multiple environment appliances by using a control command corresponding to the kitchen environment management mode, wherein the multiple environment appliances are registered in a user account and cooperate over a network.

In various embodiments of the present disclosure, the method may further include: executing a warning mode when the at least one among the gas, the oil mist, and the smoke detected by the sensor is equal to or greater than a predetermined threshold value; and controlling the cooking appliance so that output of the cooking appliance is decreased.

In various embodiments of the present disclosure, the method may further include: providing, by the server, a user terminal with a warning message in the warning mode; and outputting, by the user terminal, the warning message.

In various embodiments of the present disclosure, the method may further include: photographing the cooking appliance through a camera installed at the range hood; and transmitting an image of the cooking appliance photographed by the camera to the server.

In various embodiments of the present disclosure, the determining, by the server, of whether to execute the kitchen environment management mode may include: detecting a change in the information on the atmosphere environment by using a learning model in which the image of the cooking appliance and the information on the atmosphere environment are previously stored.

In various embodiments of the present disclosure, the method may further include: acquiring, by the camera placed above the cooking appliance, an image of cookware with which cooking is performed; and estimating, by the server, a degree of pollution of the cookware by using a pollution degree model of the cookware in which the image of the cookware and a variation of the atmosphere environment are previously stored.

In various embodiments of the present disclosure, the multiple environment appliances may include an air purifier or an air conditioner, and the driving of the multiple environment appliances by using the control command corresponding to the kitchen environment management mode may include: generating the control command for increasing output of the air purifier or the air conditioner and providing the control command to the environment appliance.

Details of other embodiments are included in the detailed description and the drawings.

The integrated management system for the kitchen environment using artificial intelligence according to the embodiments of the present disclosure automatically controls the environment appliances cooperating over the network according to the change in the kitchen environment, thereby maintaining the pleasant atmosphere environment of the kitchen.

In addition, while the change in the atmosphere environment of the kitchen is detected through the camera attached to the range hood, the degree of pollution of the cookware is identified and the control command is provided to the dishwasher, thereby enhancing the user experience of the environment appliance and dish washing.

Multiple home appliances are controlled by determining an integrated control mode appropriate for user's preference characteristics, thereby enhancing the user experience of the home appliance 300.

Effects that may be obtained from the present disclosure will not be limited to only the above described effects. In addition, other effects which are not described herein will become apparent to those skilled in the art from the following description.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
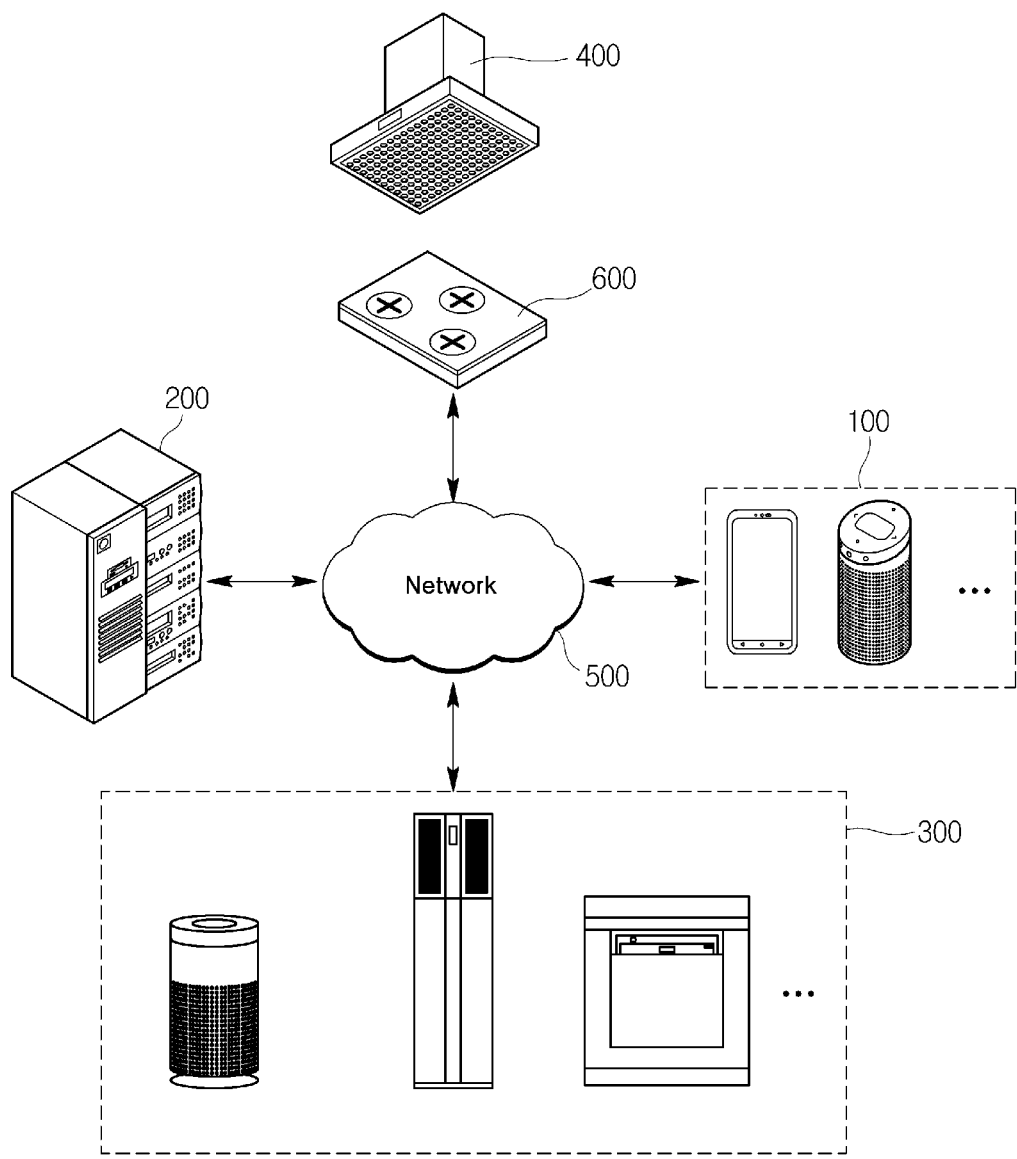
FIG. 1 is a diagram showing an integrated management system for a kitchen environment using artificial intelligence according to several embodiments of the present disclosure.

Hereinafter, embodiments described in the specification will be described in detail with reference to the accompanying drawings. Regardless of reference numerals, the same or similar elements are denoted by the same reference numerals, and a duplicated description thereof will be omitted. The suffix "module" and "unit" for the element used in the following description is merely intended to facilitate description of the specification, and the suffix itself does not have a meaning or function distinguished from others. In addition, in describing the embodiments described in the specification, if it is decided that the detailed description of the known art related to the present disclosure makes the subject matter of the present disclosure unclear, the detailed description will be omitted. In addition, the accompanying drawings are only to easily understand an embodiment described in the specification. It is to be understood that the technical idea described in the specification is not limited by the accompanying drawings, but includes all modifications, equivalents, and substitutions included in the spirit and the scope of the present disclosure.

Terms including ordinal numbers, such as "first", "second", etc. can be used to describe various elements, but the elements are not to be construed as being limited to the terms. The terms are only used to differentiate one element from other elements.

It will be understood that when an element is referred to as being "coupled" or "connected" to another element, it can be directly coupled or connected to the other element or intervening elements may be present therebetween. In contrast, it will be understood that when an element is referred to as being "directly coupled" or "directly connected" to another element, there are no intervening elements present.

FIG. 1 is a diagram showing an integrated management system for a kitchen environment using artificial intelligence according to several embodiments of the present disclosure.

An integrated management system 1 for a kitchen environment includes a configuration in which a user terminal (user equipment) 100, a server 200, a range hood 400, and a cooking appliance 600 are connected over a network 500. The user terminal 100 is for controlling an environment appliance 300. The server 200 is for determining the execution of a kitchen environment management mode and controlling the environment appliance 300. The cooking appliance 600 is for cooking food. The range hood 400 detects changes in an atmosphere environment during operation of the cooking appliance 600.

The kitchen environment management mode described in this specification refers to a mode in which the atmosphere environment in a kitchen is improved by controlling multiple environment appliances that are registered in a user account and cooperate over the network 500, or in which an operation of a dishwasher washing cookware used for cooking is controlled.

Examples of the user terminal 100 may include a mobile phone, a smart phone, a tablet PC, Ultrabook, a wearable device (for example, a watch-type artificial intelligence device (smartwatch), a glass-type artificial intelligence device (smart glass), a head mounted display (HMD)), and the like.

The user terminal 100 will be described later in detail with reference to FIG. 5.

The server 200 may provide various services related to an artificial intelligence model to the user terminal 100 in connection with an artificial intelligence model described in an embodiment of the present disclosure.

According to several embodiments of the present disclosure, the server 200 included in the integrated management system for the kitchen environment may use artificial intelligence (AI) in connection with the execution of an integrated management mode.

Artificial intelligence refers to the field of researching artificial intelligence or the methodology to create the same, and machine learning refers to the field of defining various problems in the field of artificial intelligence and researching the methodology for solving the problems. Machine learning is defined as an algorithm that improves the performance of an operation by performing a consistent experience for the operation.

An artificial neural network (ANN) is a model used in machine learning, and may refer to an overall model having a problem-solving ability, which is composed of artificial neurons (nodes) constituting a network through synaptic coupling. The artificial neural network may be defined by the followings: a connection pattern between neurons in different layers; a learning process of updating a model parameter; and an activation function generating an output value.

The artificial neural network may include an input layer, an output layer, and optionally one or more hidden layers. Each layer may include one or more neurons, and the artificial neural network may include a synapse that connects neurons. In the artificial neural network, each neuron may output a function value of an activation function for input signals input through a synapse, a weight, and a bias.

The model parameter refers to a parameter determined through learning, and includes a weight of a synapse connection, a bias of a neuron, and the like. In addition, a hyper-parameter refers to a parameter that needs to be set in a machine learning algorithm before performing learning, and includes a learning rate, the number of times for repetition, a size of a mini-batch, an initialization function, and the like.

An objective of performing learning by an artificial neural network is to determine a model parameter that minimizes a loss function. The loss function may be used as an index for determining an optimum model parameter in a learning process of the artificial neural network.

Machine learning may be classified into supervised learning, unsupervised learning, and reinforcement learning according to a learning method.

Supervised learning may refer to a method of making an artificial neural network learn, with a label provided which is related to learning data. The label may refer to a right answer (or result value) that should be estimated by the artificial neural network when the learning data is input to the artificial neural network. Unsupervised learning may refer to a method of making an artificial neural network learn, without a label provided which is related to learning data. Reinforcement learning may refer to a learning method in which an agent defined under a particular environment learns to select an action or a sequence of actions for maximizing an accumulated reward in each state.

Machine learning implemented in a deep neural network (DNN) including multiple hidden layers, among artificial neural networks, is referred to as deep learning, and the deep learning is a part of the machine learning. Hereinafter, machine learning is used as including deep learning.

In addition, the user terminal 100 included in the integrated management system for the kitchen environment according to several embodiments of the present disclosure may use the above-described artificial intelligence.

In this specification, the server 200 is described as referring to a set of computers that are connected over the network 500 and installed at a place other than the home. However, the server 200 of the present disclosure is not limited to this technical concept. Examples of the server 200 may include a device, such as a home server, a home hub, a home gateway, and the like, installed in the home.

In the case where the server 200 is a home server installed in the home, the network 500 may be a wireless network installed in the home, for example, Wi-Fi.

The environment appliance 300 is a type of embedded system, and may receive a control command from the server 200 through a wireless communication function, and may perform each function, accordingly.

In various embodiments of the present disclosure, examples of the environment appliance 300 may include, for example, an air conditioner, an air purifier, a dishwasher, and the like, but are not limited thereto.

The network 500 may be any appropriate communication network including wired and wireless networks, for example, a local area network (LAN), a wide area network (WAN), the Internet, an intranet, and an extranet; a mobile network, for example, a cellular network, 3G, LTE, 5G, Wi-Fi, and an AD-HOC network; and combination thereof.

The network 500 may include connection of network elements, such as a hub, a bridge, a router, a switch, and a gateway. The network 500 may include one or more connected networks, for example, a multi-network environment, including a public network, such as the Internet, and a private network, such as a secure private network of a corporation. Access to the network 500 may be provided over one or more wired or wireless access networks.

The user terminal 100 may transmit and receive data to the server 200, which is a learning device, over a 5G network. The user terminal 100 may perform data communication with the server 200 over the 5G network by using at least one service among enhanced mobile broadband (eMBB), ultra-reliable and low latency communications (URLLC), and massive machine-type communications (mMTC).

The enhanced mobile broadband (eMBB) is a mobile broadband service through which multimedia contents, wireless data access, and the like are provided. In addition, more enhanced mobile services such as hot spot, broadband coverage, and the like for handling explosively increasing mobile traffic may be provided through the eMBB. Through the hot spot, a large amount of traffic is handled in an area with low user mobility and high density. Through the broadband coverage, a wide and stable wireless environment and user mobility may be guaranteed.

The ultra-reliable and low latency communications (URLLC) service defines much stricter requirements than the existing LTE in terms of reliability of data transmission and reception and transmission delay. The URLLC service corresponds to a 5G service for production process automation in industrial sites, telemedicine, telesurgery, transportation, security, and the like.

The massive machine-type communications (mMTC) is a service that requires transmission of a relatively small amount of data and is not sensitive to transmission delay. Much more terminals, such as sensors, and the like, than general mobile phones may access a wireless access network simultaneously by the mMTC. In this case, costs of the communication modules of the terminals need to be cheap, and improved power efficiency or power saving technology are required so that the terminals may operate for years without battery replacement and recharging.

Figure 2:
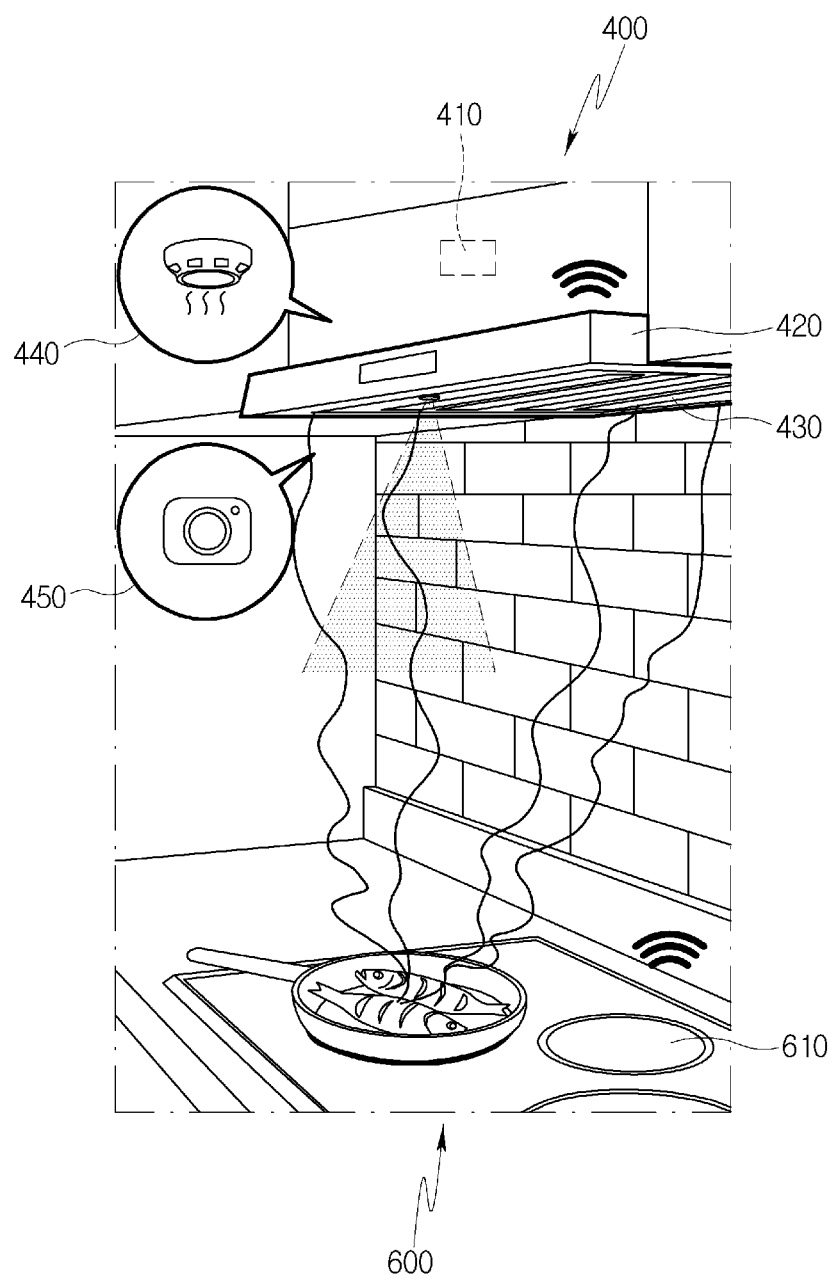
FIG. 2 is a diagram showing a range hood and a cooking appliance included in an integrated management system for a kitchen environment according to several embodiments of the present disclosure.

FIG. 2 is a diagram showing a range hood and a cooking appliance included in an integrated management system for a kitchen environment according to several embodiments of the present disclosure.

Referring to FIG. 2, the range hood 400 may include a controller 410, a communication unit 420, a fan 430, a sensor 440, and a camera 450. The cooking appliance 600 may include a heater 610.

The range hood 400 may be placed above the cooking appliance 600 to discharge the air polluted due to gas, oil mist, smoke, or the like generated during cooking, to the outside by driving the fan 430.

The controller 410 may control the communication unit 420, the fan 430, the sensor 440, and the camera 450 included in the range hood 400.

The communication unit 420 may transmit, to the server 200, information on a variation of the atmosphere environment detected by the sensor 440 or an image of a cooking appliance taken by the camera 450. The communication unit 420 may be connected to the server 200, a user terminal 210, and the like through, for example, well-known wired and wireless network technologies The fan 430 may be driven under the control of the controller 410 to discharge the polluted air to the outside. The range hood 400 may include a suction fan sucking the polluted air through a duct, and a discharge fan discharging air to the outside of the duct.

The sensor 440 may detect the change of the atmosphere environment in the kitchen when the cooking appliance 600 is used. The sensor 440 may include, for example, gas, oil mist, and smoke sensors, but the present disclosure is not limited thereto.

The camera 450 may be attached to a surface of the range hood 400 facing the cooking appliance 600, that is, a bottom surface of the range hood 400, and may acquire images of the cooking appliance 600 and cookware placed on the cooking appliance 600 during operation of the cooking appliance 600. The camera 450 may acquire images of the cooking appliance 600 at regular intervals, and may thus acquire multiple images, but no limitation thereto is imposed. That is, the cooking appliance 600 may be photographed in the form of a video.

The range hood 400 may detect the atmosphere environment changing due to the operation of the cooking appliance 600, by using the sensor 440 and the camera 450. Specifically, the sensor 440 may detect a change in numerical value of at least one among gas, oil mist, and smoke. Alternatively, the range hood 400 may acquire an image of the cooking appliance 600 by using the camera 450, and may transmit the image to the server 200. The change of the atmosphere environment may be detected by the server 200 through an analysis of the image.

The cooking appliance 600 may perform a cooking function by applying heat to the cookware placed on the heater 610. Examples of the cooking appliance 600 may include, for example, a gas stove, an induction cooktop, and the like. The heater 610 of the cooking appliance 600 may generate heat by using gas, may generate heat by applying power to a hot wire positioned on the surface of the cooking appliance 600, or may heat the cookware by using an induced current generated due to an electromagnetic induction phenomenon.

From food being cooked when heat is applied from the cooking appliance 600, gas, oil mist, and the like are generated, which may affect the kitchen environment. Alternatively, when the object to be cooked includes liquid such as soup, spillover may occur. According to an embodiment of the present disclosure, the range hood 400 may detect the generated gas and oil mist by using the sensor 440, or may detect spillover or pollution of the cookware occurring on the cooking appliance 600, by using the camera 450.

Figure 3:
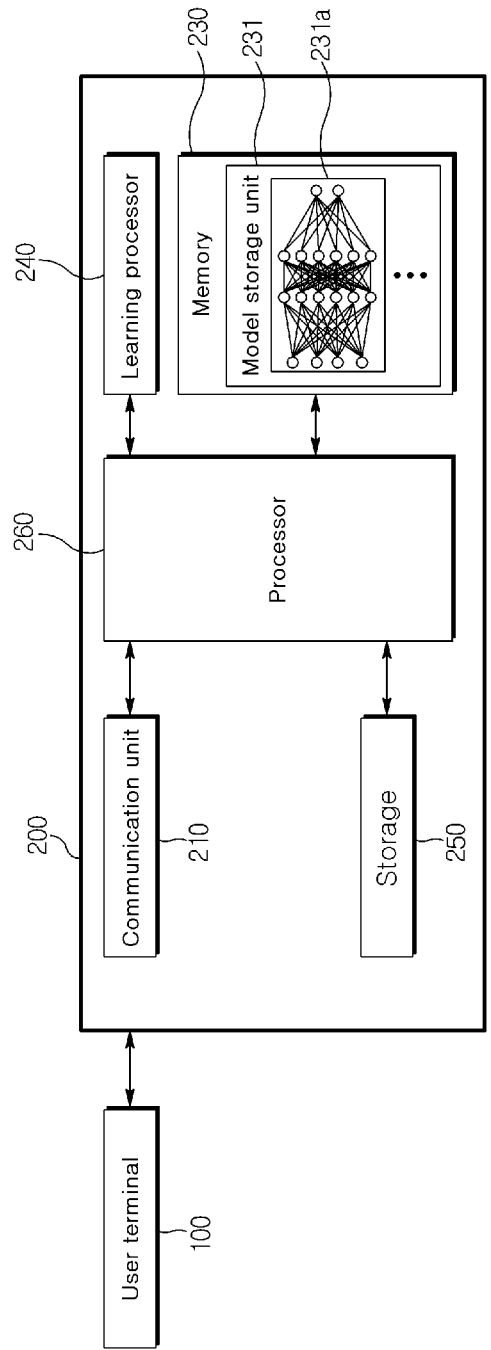
FIG. 3 is a diagram showing a server included in an integrated management system for a kitchen environment using artificial intelligence according to several embodiments of the present disclosure.

FIG. 3 is a diagram showing a server included in an integrated management system for a kitchen environment using artificial intelligence according to several embodiments of the present disclosure.

Referring to FIG. 3, the server 200 may include a communication unit 210, an input unit 220, a memory 230, a learning processor 240, a storage 250, a processor 260, and the like.

The communication unit 210 may transmit and receive data to other devices through wired/wireless communication or an interface.

The input unit 220 is a component corresponding to an input unit 120 of FIG. 2, and may acquire data by receiving data through the communication unit 210.

The input unit 220 may acquire input data, and the like for acquiring output by using training data for model learning and a trained model.

The input unit 220 may acquire raw input data. In this case, the processor 260 may preprocess the acquired data to generate training data which may be input for model learning, or preprocessed input data.

Herein, preprocessing for the input data performed by the input unit 220 may refer to extracting an input feature point from the input data.

The memory 230 may include a model storage unit 231, a database 232, and the like. The memory 230 may temporarily store data processed by the processor 260.

The model storage unit 231 stores a model that is in the middle of learning through the learning processor 240, or a trained model (or an artificial neural network 231a). When the model is updated through learning, the model storage unit 231 stores the updated model. As will be described later, the trained model 231a may be used to analyze the variation of the atmosphere environment and the image of the cooking appliance 600 acquired from the range hood 400.

Herein, when necessary, the model storage unit 231 may store the trained model in multiple versions divided according to a learning time point, a learning progress degree, or the like.

The artificial neural network 231a shown in FIG. 3 is merely an example of an artificial neural network including multiple hidden layers, and the artificial neural network of the present disclosure is not limited thereto.

The artificial neural network 231a may be implemented in hardware, software, or combination thereof. When a part or the entire of the artificial neural network 231a is implemented in software, one or more instructions constituting the artificial neural network 231a may be stored in the memory 230.

The database 232 may store the input data acquired by the input unit 220, learning data (or training data) used for model learning, learning history of a model, and the like.

The input data stored in the database 232 may be data processed to be appropriate for model learning, as well as raw input data itself.

The server 200 included in the integrated management system of the kitchen environment according to several embodiments of the present disclosure may store user account information. The user account information stored in the server 200 will be described later in detail with reference to FIG. 7.

The learning processor 240 may make the artificial neural network 231a train (or learn) using training data or a training set.

The learning processor 240 may be configured to perform data mining, a data analysis, intelligent decision making, and a machine learning algorithm, and to receive, classify, store, and output information to be used for the technologies.

The learning processor 240 may include one or more memory units configured to store data that is received, detected, sensed, generated, predefined, or differently output by the server 200; or data that is received, detected, sensed, generated, predefined, or differently output by another component, device, server 200, or a device communicating with the server 200.

Generally, the learning processor 240 may be configured to store data in one or more databases to identify, index, categorize, manipulate, store, fine, and output data for use in supervised or unsupervised learning, data mining, predictive analytics, or other machines.

The information stored in the learning processor 240 may be used by the processor 260, using any of different types of data analysis algorithms and machine learning algorithms.

Examples of such algorithms includes a k-nearest neighbor system, fuzzy logic (for example, possibility theory), a neural network, a Boltzmann machine, vector quantization, a pulsed neural network, a support vector machine, a maximum margin classifier, hill climbing, an inductive logic system, a Bayesian network, a Petri net (for example, a finite state machine, a mealy machine, and a Moore finite state machine), a classifier tree (for example, a perceptron tree, a support vector tree, a Markov tree, a decision tree forest, and a random forest), pandemonium model and system, artificial fusion, sensor fusion, image fusion, reinforcement learning, augmented reality, pattern recognition, automated planning, and the like.

The learning processor 240 may directly acquire the data preprocessed from the input data acquired by the processor 260 through the input unit 220 so as to perform learning for the artificial neural network 231a, or may acquire the preprocessed input data stored in the database 232 so as to perform learning for the artificial neural network 231a.

Specifically, the learning processor 240 may repeatedly make the artificial neural network 231a learn with the above-described various learning techniques, thereby determining the optimized model parameters of the artificial neural network 231a.

In this specification, an artificial neural network of which a parameter is determined by performing learning with training data may be referred to as a learning model or trained model.

Herein, the learning model may infer a result value while being loaded in the server 200 of the artificial neural network, or may be transmitted to another device, such as the user terminal 100, through the communication unit 210 and may be loaded in the device.

In addition, when the learning model is updated, the updated learning model is transmitted to another device, such as the user terminal 100, through the communication unit 210 and loaded in the device.

The storage 250 may store a program and data required for the operation of the server 200. For example, the storage 250 may store program data related to a control command corresponding to an integrated management mode of an environment appliance, and when the program is executed by the processor 260, the storage 250 provides the program data to the memory 230.

In addition, the storage 250 may store data related to a user account and information on an environment appliance registered for each user. As will be described later, the server 200 may load the information on the environment appliance registered in the user account. Herein, the processor 260 may load the information on the environment appliance registered in the user account, from the storage 250, and may provide the information to the memory 230.

In addition, the server 200 may evaluate the artificial intelligence model. After the evaluation, the server 200 may update the artificial intelligence model for better performance, and may provide the updated artificial intelligence model to the user terminal 100. Herein, the user terminal 100 may perform a series of steps performed by the server 200, in a local area alone or through communication with the server 200 together.

For example, the user terminal 100 may make the artificial intelligence model learn a user's personal pattern through learning of user's personal data, thereby updating the artificial intelligence model downloaded from the server 200.

Figure 4:
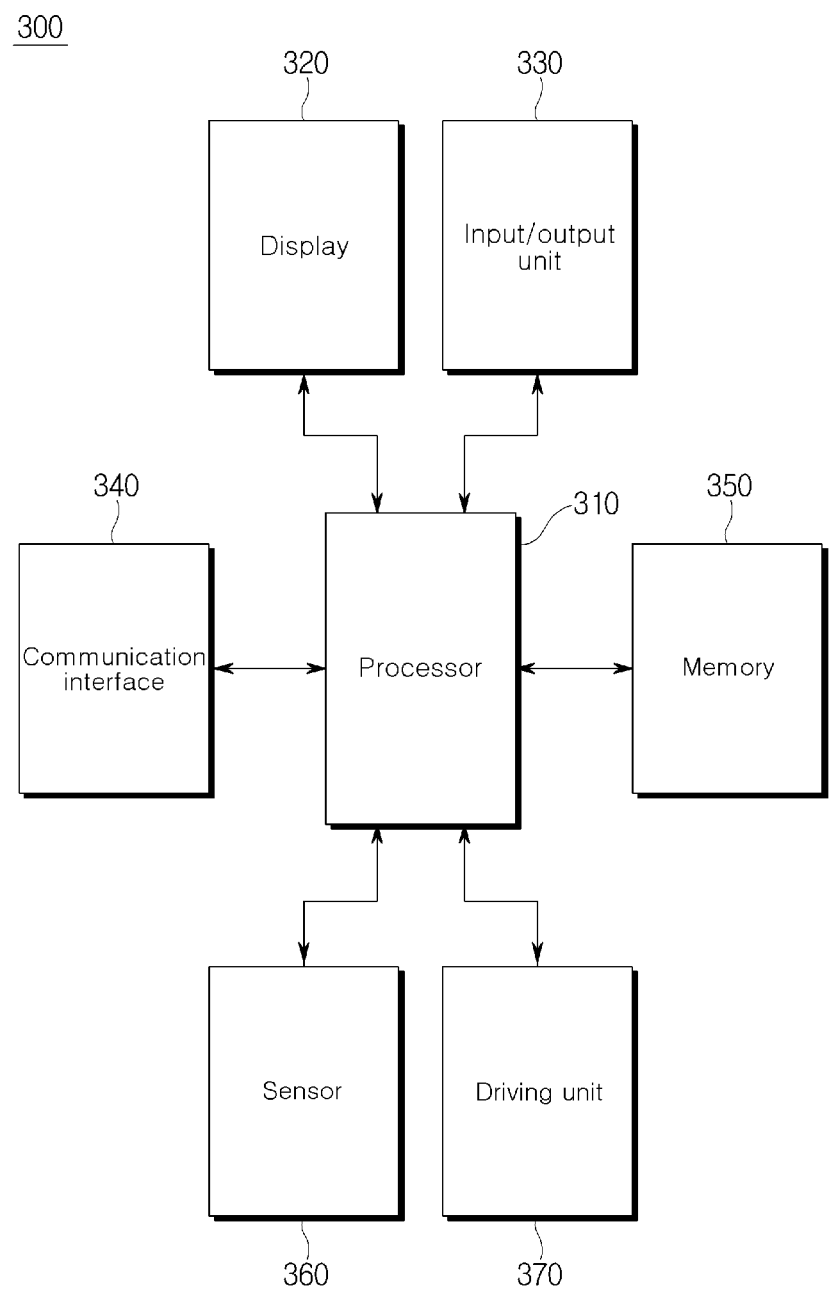
FIG. 4 is a diagram showing an environment appliance included in an integrated management system for a kitchen environment using artificial intelligence according to several embodiments of the present disclosure.

FIG. 4 is a diagram showing an environment appliance included in an integrated management system for a kitchen environment using artificial intelligence according to several embodiments of the present disclosure.

Examples of the environment appliance 300 may include an air conditioner, an air purifier, and a dishwasher. The environment appliance 300 may be driven by receiving a control command from the server 200.

The environment appliance 300 may include a processor 310, a display 320, an input/output unit 330, a communication interface 340, a memory 350, a sensor 360, and a driving unit 370.

The processor 310 may control the operation of the environment appliance 300. Specifically, when a control command of the environment appliance 300 is provided through the communication interface 340 connected to the user terminal 100 or the server 200, the processor 310 controls the operation of the environment appliance 300 on the basis of the control command.

The display 320 may display an internal state or data of the environment appliance 300. In several embodiments, the user may control the environment appliance 300 through a user interface displayed on the display 320.

The input/output unit 330 may include at least one among an input unit, such as a camera for video signal input, a microphone for receiving an audio signal, and the like; and/or a sound output unit, a haptic module, and an optical output unit that are output units for generating output related to visual, auditory, tactile senses, and the like.

The communication interface 340 may include a transmitter and a receiver. The environment appliance 300 may be connected to the user terminal 100 or the server 200 by accessing the network 500 through the communication interface 340.

The environment appliance 300 connected to the user terminal 100 or the server 200 may receive a control command required for driving the environment appliance 300, through the communication interface 340.

The communication interface 340 may use, for example, a wireless Internet standard, such as a wireless LAN (WLAN), Wi-Fi, Wi-Fi Direct, Digital Living Network Alliance (DLNA), wireless broadband (WiBro), World Interoperability for Microwave Access (WiMAX), High Speed Downlink Packet Access (HSDPA), High Speed Uplink Packet Access (HSUPA), Long Term Evolution (LTE), Long Term Evolution-Advanced (LTE-A), and the like, but the present disclosure is not limited to the above-described examples of the wireless Internet technical standards.

The memory 350 may include a volatile memory or a non-volatile memory. Examples of the non-volatile memory include read-only memory (ROM), a programmable ROM (PROM), an electrically programmable ROM (EPROM), an electrically erasable and programmable ROM (EEPROM), flash memory, phase-change RAM (PRAM), magnetic RAM (MRAM), resistive RAM (RRAM), ferroelectric RAM (FRAM), etc. The volatile memory may include at least one of various memories, such as dynamic RAM (DRAM), static RAM (SRAM), synchronous DRAM (SDRAM), phase-change RAM (PRAM), magnetic RAM (MRAM), resistive RAM (RRAM), ferroelectric RAM (Fe-RAM), etc.

Examples of the sensor 360 may include a proximity sensor, an illumination sensor 142, a touch sensor, an acceleration sensor, a magnetic sensor, a gravity sensor (G-sensor), a gyroscope sensor, a motion sensor, an RGB sensor, an infrared sensor (IR sensor), a finger scan sensor, an ultrasonic sensor, an optical sensor, and the like, but are not limited thereto.

For example, in the case where the environment appliance 300 is an air conditioner, the sensor 360 may be a temperature sensor for measuring the temperature of the air around the air conditioner. Alternatively, in the case where the environment appliance 300 is an air purifier, the sensor 360 may be a fine-dust sensor or odor sensor for measuring the degree of pollution of the air around the air purifier.

In the case where the environment appliance 300 is a dishwasher, the sensor 360 may be a temperature sensor measuring the temperature of the wash water.

It is described that the driving unit 370 refers to a part that provides mechanical movement or electrical movement required for driving of various environment appliances (an air conditioner, an air purifier, a dishwasher, and the like) described below.

For example, in the case where the environment appliance 300 is an air conditioner, the driving unit 370 may include a compressor for generating cold air. Alternatively, in the case where the environment appliance 300 is an air purifier, the driving unit 370 may include a fan. In the case where the environment appliance 300 is a dishwasher, the driving unit 370 may include a pump spouting the wash water, and the like.

Figure 5:
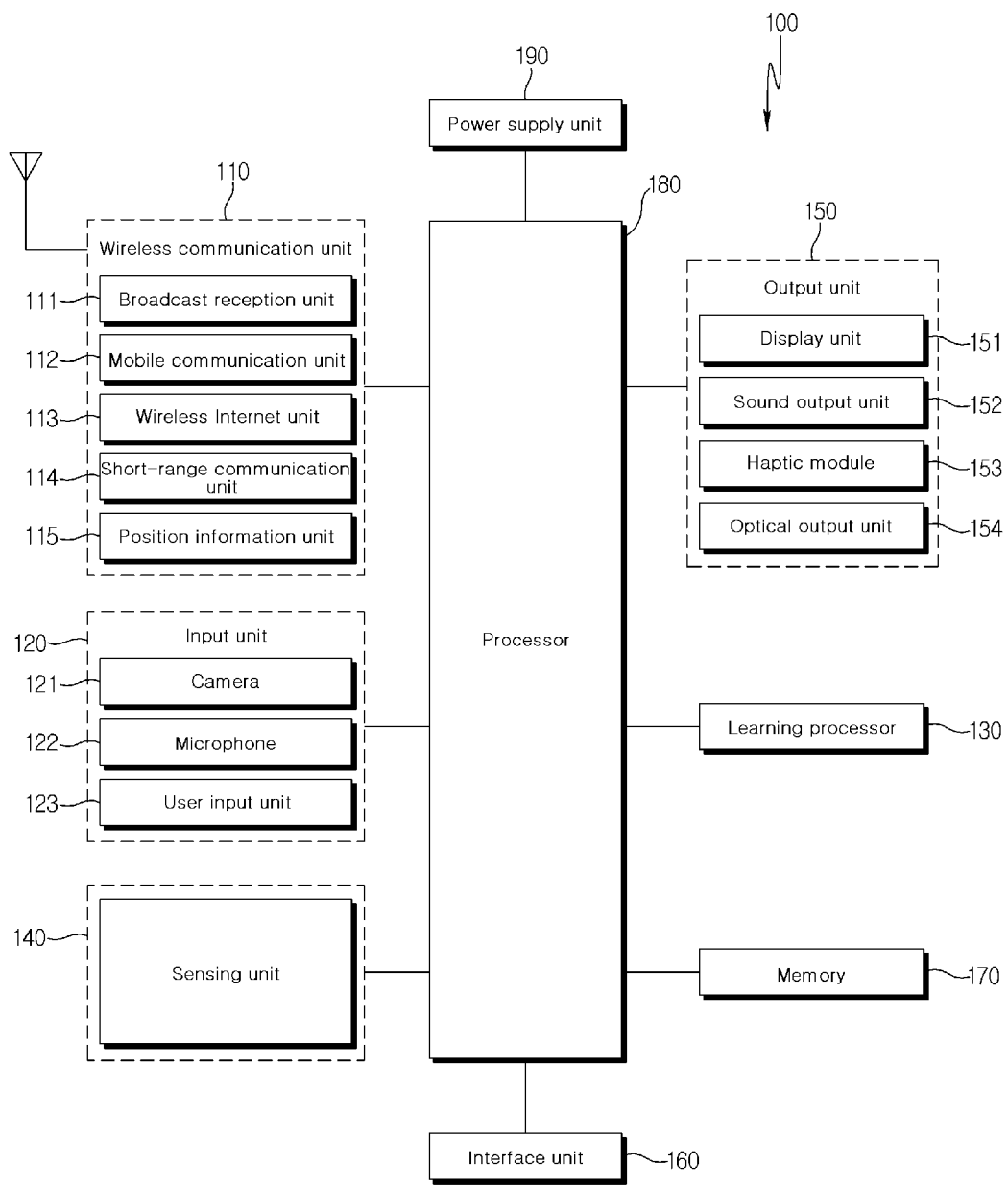
FIG. 5 is a diagram showing a user terminal included in an integrated management system for a kitchen environment using artificial intelligence according to several embodiments of the present disclosure.

FIG. 5 is a diagram showing a user terminal included in an integrated management system for a kitchen environment using artificial intelligence according to several embodiments of the present disclosure.

The user terminal 100 included in the integrated management system for the kitchen environment according to an embodiment of the present disclosure may perform a function of a control terminal for controlling the environment appliance 300. The environment appliance 300 may receive a control command corresponding to a kitchen environment management mode through the user terminal 100, and may perform an operation according to the control command.

A wireless communication unit 110 may include at least one among a broadcast reception unit 111, a mobile communication unit 112, a wireless Internet unit 113, a short-range communication unit 114, and a position information unit 115.

The broadcast reception unit 111 may receive a broadcast signal and/or broadcast-related information from an external broadcast management server through a broadcast channel.

The mobile communication unit 112 may transmit and receive a wireless signal from at least one among a base station, an external terminal, and a server over a mobile communication network that are established according to technical standards or communications methods for mobile communication (for example, The Global System for Mobile communication (GSM), code-division multiple access (CDMA), code-division multiple access 2000 (CDMA2000), Enhanced Voice-Data Optimized or Enhanced Voice-Data Only (EV-DO), Wideband CDMA (WCDMA), High Speed Downlink Packet Access (HSDPA), High Speed Uplink Packet Access (HSUPA), Long Term Evolution (LTE), Long Term Evolution-Advanced (LTE-A), and the like). However, the present disclosure is not limited to the above-described examples of the communication methods.

The wireless Internet unit 113 is a module for wireless Internet access, and may be built in the user terminal 100 or provided as an external module. The wireless Internet unit 113 may be configured to transmit and receive wireless signals over a communication network according to wireless Internet technologies.

Examples of the wireless Internet technologies include a wireless LAN (WLAN), Wi-Fi, Wi-Fi Direct, Digital Living Network Alliance (DLNA), wireless broadband (WiBro), World Interoperability for Microwave Access (WiMAX), High Speed Downlink Packet Access (HSDPA), High Speed Uplink Packet Access (HSUPA), Long Term Evolution (LTE), Long Term Evolution-Advanced (LTE-A), and the like. However, the present disclosure is not limited to the above-described examples of the wireless Internet technical stands.

The short-range communication unit 114 is for short-range communication, and may support short-range communication by using at least one among Bluetooth™, radio-frequency identification (RFID), Infrared Data Association (IrDA), ultra-wideband (UWB), ZigBee, near-field communication (NFC), Wi-Fi, Wi-Fi Direct, Wireless Universal Serial Bus (Wireless USB) technologies. However, the present disclosure is not limited to the above-described examples of the short-range communication methods.

The position information unit 115 is a module for acquiring the position (or current position) of the user terminal 100, and representative examples of the position information unit include a Global Positioning System (GPS) module or a Wi-Fi module. For example, using the GPS module, the user terminal 100 may acquire the position of the user terminal 100 by using a signal transmitted from a GPS satellite.

The input unit 120 may include a camera 121 for inputting an image signal, a microphone 122 for receiving an audio signal, and a user input unit 123 for receiving information from a user.

Speech data or image data collected by the input unit 120 may be analyzed by the processor 180 to be processed as a user's control command.

The input unit 120 is for input of video information (or signal), audio information (or signal), data, or information input from the user. For input of the video information, the user terminal 100 may include one or multiple cameras 121.

The camera 121 processes image frames such as still images, video, or the like acquired by an image sensor in a video call mode or a shooting mode. The processed image frame may be displayed on a display unit 151 or stored in a memory 170.

The microphone 122 processes external sound signals into electrical speech data. The user terminal 100 may receive a user's speech command through the microphone 122.

The processed speech data may be used in various ways depending on the function being performed (or an application program in execution) by the user terminal 100. In the meantime, in the microphone 122, various noise-removal algorithms for removing noise that occurs in the process of receiving an external sound signal may be implemented.

The user input unit 123 is for receiving information from a user. When information is input through the user input unit 123, the processor 180 controls the operation of the user terminal 100 according to the input information. The user input unit 123 may include a touch input means and a mechanical input means (or a mechanical key, for example, a button, a dome switch, a jog wheel, a jog switch, etc. positioned on the front/rear or the side of the mobile terminal 100).

For example, the touch input means may include a virtual key, a soft key, or a visual key displayed on the display unit 151 through software processing, or may include a touch key placed on a portion other than the display unit 151. In the meantime, the virtual key or visual key may have various forms and may be displayed on a touch screen. For example, the virtual key or visual key may be formed of a graphic, text, icon, video, or a combination thereof.

The learning processor 130 may include a configuration corresponding to the learning processor 240 of FIG. 3. The learning processor 130 may be configured to perform data mining, a data analysis, intelligent decision making, and a machine learning algorithm, and to receive, classify, store, and output information to be used for the technologies.

The processor 180 may actively elicit and acquire information required to fully determine the requirements on the basis of the contextual condition or the user's intent. For example, the processor 180 may actively elicit information required to determine the requirements, by analyzing historical data that includes historical input and output, pattern matching, unambiguous words, input intent, etc.

The processor 180 may determine a flow of tasks for executing a function that responds to the requirements on the basis of the contextual condition or the user's intent.

The processor 180 may be configured to collect, sense, extract, detect, and/or receive a signal or data used for a data analysis and machine learning operation, through one or more sensing components in the user terminal, in order to collect information for processing and storage by the learning processor 130.

Collection of information may include sensing information through a sensor, extracting information stored in the memory 170, or receiving information from another artificial intelligence device, entity, or external storage device through a communication means.

The processor 180 may collect and store use history information of a user terminal of the present disclosure. The processor 180 may determine the best match for performing a particular function, by using the stored use history information and predictive modeling.

The processor 180 may receive or sense the information on the surrounding environment or other types of information through the sensing unit 140.

The processor 180 may receive a broadcast signal and/or broadcast-related information, a wireless signal, and wireless data through the wireless communication unit 110.

The processor 180 may receive image information (or a signal corresponding thereto), audio information (or a signal corresponding thereto), data, or user input information from the input unit 120.

The processor 180 may collect information in real time, may process or classify information (for example, a knowledge graph, a command policy, a personalization database, a dialogue engine, etc.), and may store the processed information in the memory 170 or the learning processor 130.

When the operation of the user terminal 100 is determined on the basis of a data analysis, and machine learning algorithm and technology, the processor 180 controls the elements of the user terminal 100 so as to execute the determined operation. The processor 180 may then perform the determined operation by controlling the terminal according to a control command.

When a particular operation is performed, the processor 180 analyzes history information indicating execution of the particular operation through a data analysis and machine learning algorithm and technique, and updates the previously-learned information on the basis of the analyzed information.

Accordingly, the processor 180, in combination with the learning processor 130, may enhance, on the basis of the updated information, the accuracy of future performance of the data analysis and the machine learning algorithm and technique.

The sensing unit 140 may include one or more sensors sensing at least one among information in the mobile user terminal 100, information on a surrounding environment around the mobile user terminal 100, and user information.

For example, the sensing unit 140 may include at least one among a proximity sensor 141, an illumination sensor 142, a touch sensor, an acceleration sensor, a magnetic sensor, a gravity sensor (G-sensor), a gyroscope sensor, a motion sensor, an RGB sensor, an infrared sensor (IR sensor), a finger scan sensor, an ultrasonic sensor, an optical sensor (for example, the camera 121), the microphone 122, a battery gauge, an environmental sensor (for example, a barometer, a hygrometer, a thermometer, a radioactivity sensor, a heat sensor, a gas sensor, etc.), and a chemical sensor (for example, an electronic nose, a healthcare sensor, a biometric sensor, etc.). In the meantime, the mobile user terminal 100 described in this specification may use a combination of information sensed by at least two sensors of these sensors.

An output unit 150 is for generating output related to visual, auditory, tactile senses, etc. and may include at least one among the display unit 151, a sound output unit 152, a haptic module 153, and an optical output unit 154.

The display unit 151 displays (outputs) information processed by the user terminal 100. For example, the display unit 151 may display execution-screen information of an application program run on the user terminal 100, or User Interface (UI) and Graphic User Interface (GUI) information according to the execution-screen information.

The display unit 151 and a touch sensor may have an inter-layered structure or may be integrated, thereby implementing a touch screen. This touch screen may serve as the user input unit 123 that provides an input interface between the user terminal 100 and the user and may provide an output interface between the user terminal 100 and the user.

The sound output unit 152 may output audio data received from the wireless communication unit 110 or stored in the memory 170, in a call signal reception mode, a call mode, a recording mode, a speech recognition mode, a broadcast reception mode, or the like. The sound output unit 152 may include at least one among a receiver, a speaker, and a buzzer.

The haptic module 153 generates various tactile effects that the user feels. A representative example of the tactile effects generated by the haptic module 153 may be vibration.

The optical output unit 154 outputs a signal for informing about the occurrence of an event, by using light of a light source of the user terminal 100. Examples of the event generated in the user terminal 100 may include receiving a message, receiving a call signal, a missed call, an alarm, schedule notification, receiving an email, receiving information through an application, and the like.

The interface unit 160 serves as a passage to various types of external devices connected to the user terminal 100. The interface unit 160 may include at least one among a wired/wireless headset port, an external-charger port, a wired/wireless data port, a memory card port, a port connecting a device equipped with an identification module, an audio input/output (I/O) port, a video input/output (I/O) port, and an earphone port. In the user terminal 100, in response to connection between an external device and the interface unit 160, appropriate control related to the connected external device may be performed.

In the meantime, the identification module is a chip storing various types of information for authenticating the use authority of the user terminal 100, and examples of the identification module may include a user identify module (UIM), a subscriber identity module (SIM), a universal subscriber identity module (USIM), or the like. A device (hereinafter, referred to as an "identification device") equipped with the identification module may be manufactured in a form of a smart card. Therefore, the identification device may be connected to the user terminal 100 through the interface unit 160.

The memory 170 may be for storing data supporting various functions of the user terminal 100.

The memory 170 may store a number of application programs or applications running on the user terminal 100, data for operation of the user terminal 100, instructions, and data (for example, at least one algorithm information for machine learning, etc.) for operation of the learning processor 130.

Like the memory 350, the memory 170 may include various types of volatile memories and non-volatile memories.

Generally, the processor 180 controls the overall operation of the user terminal 100, in addition to the operations related to the application program. The processor 180 may process input or output signals, data, information, etc. or may execute the application program stored in the memory 170 through the above-described elements, thereby providing or processing information or a function appropriate for the user.

In addition, the processor 180 may control at least one or some of the elements described with reference to FIG. 1, so as to run the application program stored in the memory 170. Further, the processor 180 may operate at least two of the elements included in the user terminal 100 in combination so as to operate the application program.

Under the control of the processor 180, the power supply unit 190 may receive external power or internal power to supply the power to each of the elements included in the user terminal 100.

The power supply unit 190 may include, for example, a battery, and the battery may be a built-in battery or a replaceable battery. Alternatively, the power supply unit 190 may an adapter that receives AC power, converts the AC power into DC power, and supplies the DC power to the user terminal 100.

In the meantime, as described above, the processor 180 controls the operations related to an application program, and generally the overall operation of the user terminal 100. For example, when a state of the user terminal 100 meets a set condition, the processor 180 may set a lock state in which input of the user's control command to applications is limited, or may stop the lock state.

Figure 6:
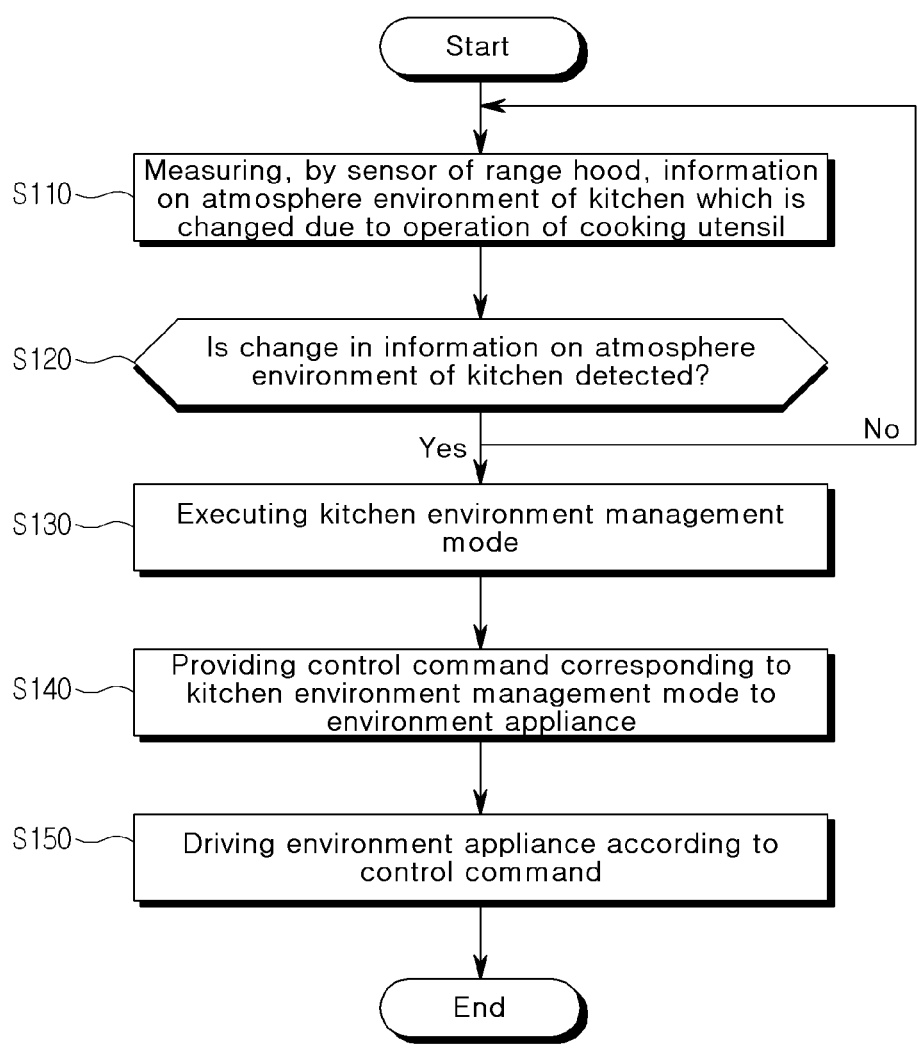
FIG. 6 is a flowchart showing an integrated management method of a kitchen environment using artificial intelligence according to several embodiments of the present disclosure.

FIG. 6 is a flowchart showing an integrated management method of a kitchen environment using artificial intelligence according to several embodiments of the present disclosure.

Referring to FIG. 6, the integrated management method of the kitchen environment using artificial intelligence according to several embodiments of the present disclosure may include measuring, by the sensor of the range hood, information on an atmosphere environment of the kitchen which is changed due to an operation of a cooking appliance, at step S110.

As described above, the range hood 400 may include the sensor 440 for sensing gas, oil mist, smoke, or the like generated by the operation of the cooking appliance 600. The sensor 440 may measure the information on the atmosphere environment of the kitchen and a change thereof, and may provide the controller 410 with information on the amount of pollutant in the air, which is included in the measured information on the atmosphere environment of the kitchen.

The range hood 400 may be connected to the server 200 over the network 500, and may transmit the measured information on the atmosphere environment of the kitchen to the server 200.

In other several embodiments of the present disclosure, the range hood 400 may not continuously transmit the information on the atmosphere environment of the kitchen or the amount of the pollutant in the air detected through the sensor 440, to the server 200. When the amount of pollutant measured by the sensor 440 exceeds a predetermined threshold value, the range hood 400 transmits information on the occurrence of the event to the server 200.

In addition, in other several embodiments of the present disclosure, the range hood 400 may acquire an image of the cooking appliance 600 by using the camera 450 so as to detect whether the information on the kitchen environment is changed. The acquired images may be transmitted to the server 200. The acquired images may be a video or a set of multiple images acquired at regular intervals.

Afterwards, it is determined whether a change in the information on the atmosphere environment of the kitchen is detected, at step S120.

The server 200 may receive the information on the atmosphere environment of the kitchen from the range hood 400, and may use this to detect the change in the information on the atmosphere environment of the kitchen. This may include determining whether the measured amount of the pollutant in the air exceeds a predetermined value.

In several embodiments, the server 200 may detect the change in the information on the atmosphere environment of the kitchen on the basis of the image acquired from the camera 450 of the range hood 400. To this end, the server 200 may previously store, in the model storage unit 231, a learning model generated by using a relationship between information on the atmosphere environment and a set of images of the cooking appliance 600 when gas, oil mist, smoke, or the like occurs.

The server 200 may provide the images provided from the range hood 400 as input data by using the stored learning model and the artificial neural network 231*a*, and may generate the information on the atmosphere environment of the kitchen as an output value. The server 200 may detect the change in the information on the atmosphere environment of the kitchen by using the information on the atmosphere environment of the kitchen which is output using the artificial neural network 231*a*.

When the change in the information on the atmosphere environment of the kitchen is detected, the server 200 executes a kitchen environment management mode at step S130. When the change in the information on the atmosphere environment of the kitchen is not detected, it is continuously determined whether the information on the atmosphere environment of the kitchen provided from the range hood 400 is changed.

When the server 200 determines to execute the kitchen environment management mode, the server 200 generates a control command corresponding to the kitchen environment management mode. The control command corresponds to a control command for controlling the environment appliance 300. The server 200 may reference the pre-stored user account information so as to generate the control command.

Figure 7:
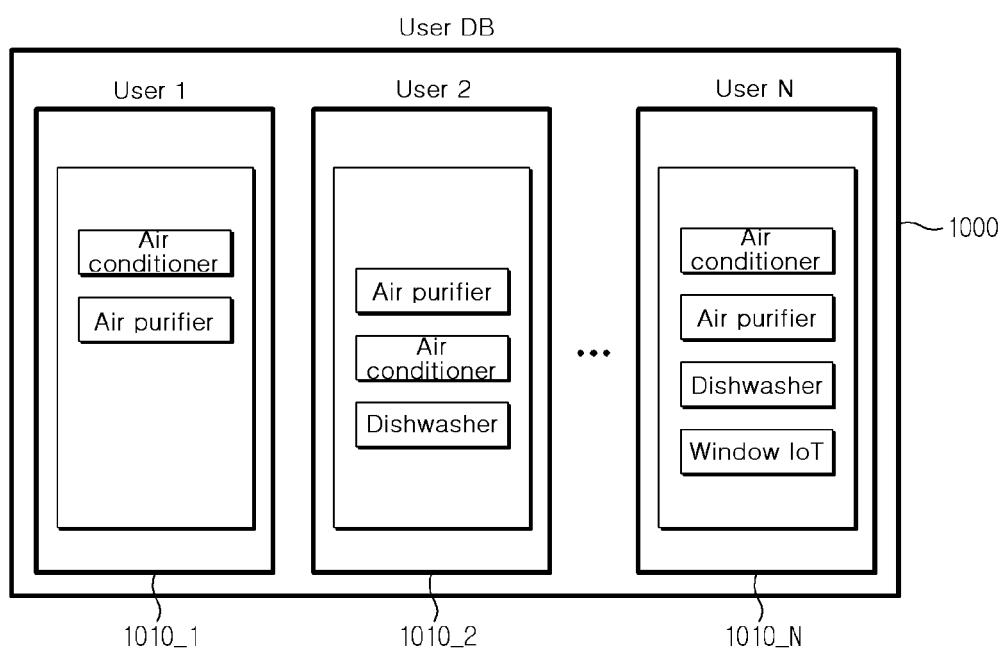
FIG. 7 is a diagram showing a user account stored in an integrated management system for a kitchen environment using artificial intelligence according to several embodiments of the present disclosure.

FIG. 7 is a diagram showing a user account stored in an integrated management system for a kitchen environment using artificial intelligence according to several embodiments of the present disclosure.

A user database 1000 may be stored in the storage 250 of the server 200. However, the present disclosure is not limited thereto. The user database 1000 may be stored in another server connected to the server 200 over the network 500.

The user database 1000 may contain data related to a user account. Each user may own a user account on the server 200, and may access data stored in the user account by logging in to its account. FIG. 7 shows an example that the user database 1000 stores accounts 1010_1 to 510_N of user 1 to user N.

In the user account, a list of environment appliances registered in the user account by each user may be stored. FIG. 7 shows an example that information of an air conditioner and an air purifier is registered in the account 1010_1 of the user 1 and information of an air conditioner, an air purifier, and a dishwasher is registered in the account 1010_2 of the user 2.

The environment appliances registered in the user account refer to environment appliances that the user may use. That is, the environment appliances are environment appliances that may operate by receiving a control command in the kitchen environment management mode executed by the server 200.

For example, when the kitchen environment management mode is executed for the environment appliance registered in the account of the user 1, the server 200 generates a control command for increasing the air flow rate of the air conditioner or the output of the air purifier for air circulation in the kitchen.

As another example, when the kitchen environment management mode is executed for the environment appliance registered in the account of the user N, the server 200 generates a control command to open a window having an IoT function.

The server 200 may provide the generated control command to the environment appliance 300. The environment appliance 300 may receive the generated control command from the server 200 through the communication interface 340.

In other several embodiments of the present disclosure, the generated control command may be provided to the user terminal 100. The user terminal 100 may receive input of the user who wants to drive the environment appliance 300, with the provided control command, and may transmit the input to the environment appliance 300.

Afterwards, the environment appliance 300 may be driven according to the received control command at step S150. The sensor of the range hood 400 may continuously measure the information on the kitchen environment while the environment appliance 300 operates according to the control command received from the server 200, and may transmit a result of the measurement to the server 200. The server 200 terminates the kitchen environment management mode when the information on the kitchen environment measured by the range hood 400 returns to normal. When the kitchen environment management mode is terminated, the environment appliance 300 continues the operation performed before the mode starts.

The integrated management system for the kitchen environment using artificial intelligence according to the embodiments of the present disclosure automatically controls the environment appliances cooperating over the network according to the change in the kitchen environment, thereby maintaining the pleasant atmosphere environment of the kitchen.

Figure 8:
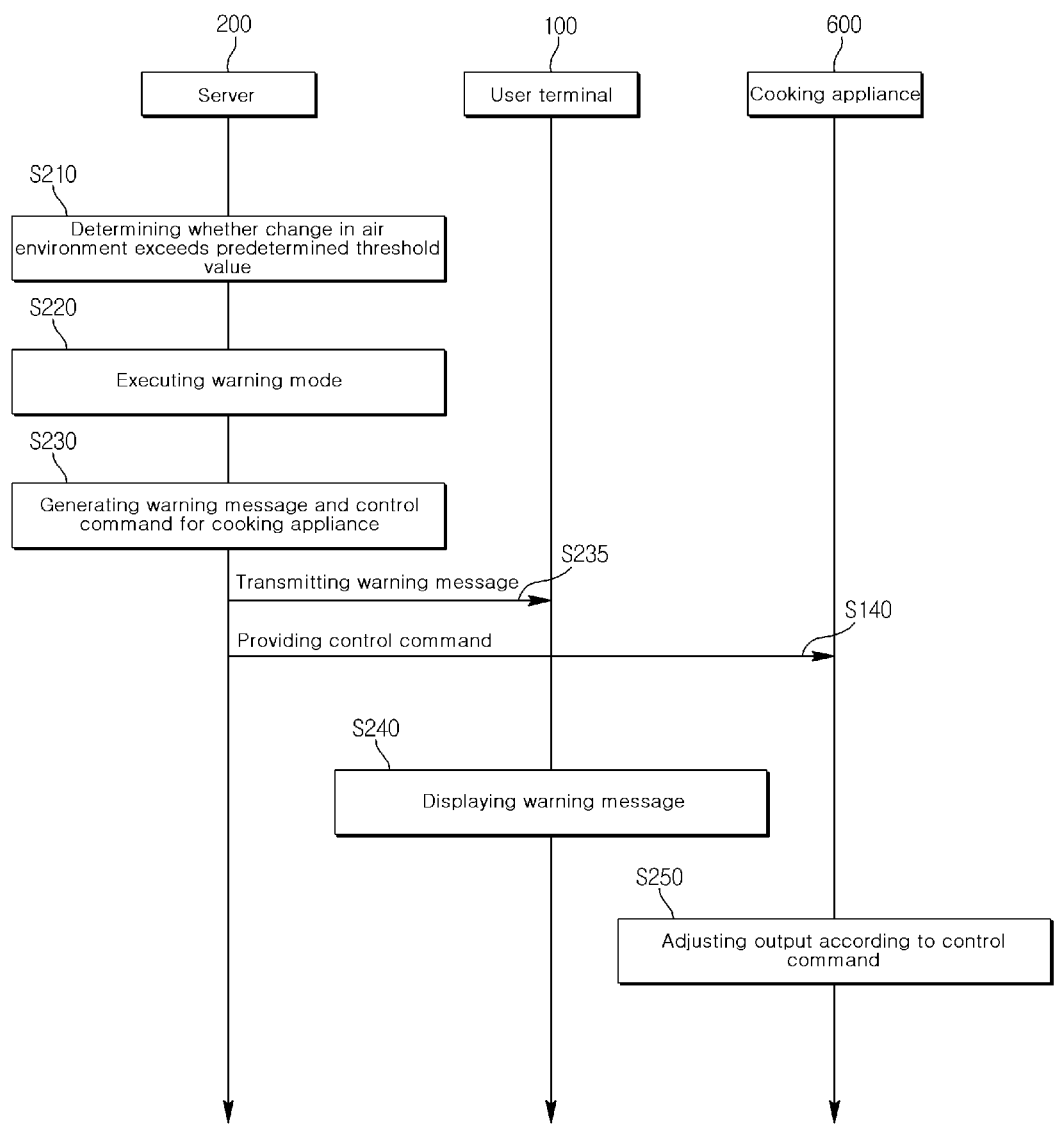
FIG. 8 is a data flowchart showing an integrated management method of a kitchen environment using artificial intelligence according to several embodiments of the present disclosure.

FIG. 8 is a data flowchart showing an integrated management method of a kitchen environment using artificial intelligence according to several embodiments of the present disclosure.

Referring to FIG. 8, it is described operation of recognizing an dangerous situation when the kitchen environment measured by the range hood 400 exceeds the predetermined threshold value, and executing a warning mode and informing the user about this.

Specifically, by using measurement data transmitted from the range hood 400, the server 200 determines whether a measurement value exceeds the predetermined threshold value at step S210. When it is determined the change in the atmosphere environment measured by the range hood 400 exceeds the predetermined threshold value, the server 200 executes the warning mode at step S220.

The warning mode is a mode for informing the user that the kitchen environment reaches a degree that may endanger the user, and for instructing the environment appliance 300 to perform an operation for solving this situation.

To this end, the server 200 generates a warning message, and a control command to be provided to the cooking appliance 600, at step S230. The control command provided to the cooking appliance 600 may include a control command for adjusting the output of the cooking appliance 600 or turning the power of the cooking appliance 600 off when necessary.

The server 200 provides the generated warning message to the user terminal 100 at step S235 while providing the control command to the cooking appliance 600 at step S236. The user terminal 100 received the warning message may output the warning message to the display unit 151 or may output the warning message into a voice or sound through the sound output unit 152 at step S240.

The cooking appliance 600 may adjust the output of the heater 610 or may turn the power off, according to the control command provided from the server 200, at step S250.

In other several embodiments of the present disclosure, the user terminal 100 displaying the warning message provided from the server 200 may receive user input so that the user may control the cooking appliance 600. For example, the user input may be a speech command input through the microphone 122, or may have the form of touch input provided through the display unit 151.

Figure 9:
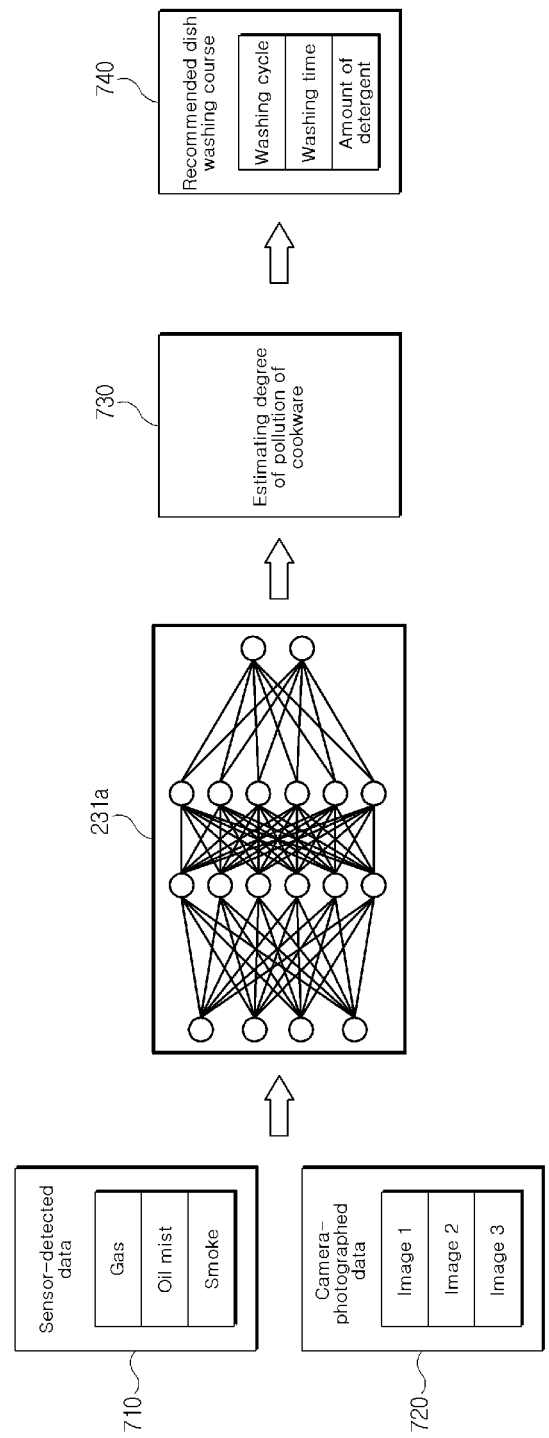
FIG. 9 is a diagram showing an operation of a dishwasher that is controlled by an integrated management system for a kitchen environment using artificial intelligence according to several embodiments of the present disclosure.

FIG. 9 is a diagram showing an operation of a dishwasher that is controlled by an integrated management system for a kitchen environment using artificial intelligence according to several embodiments of the present disclosure.

Examples of the environment appliance 300 controlled by the server 200 may include a dishwasher. The server 200 may use the information provided from the range hood 400 to generate a control command related to the washing operation of the dishwasher, and may control the dishwasher through the control command.

Specifically, the sensor 440 of the range hood 400 may provide data acquired by measuring, for example, the amount of gas, oil mist, and smoke, to the server 200. In addition, the camera 450 of the range hood 400 may acquire images of the cooking appliance 600 and the cookware during the cooking operation, and may provide the images to the server 200.

The server 200 may estimate the degree of pollution of the cookware by using data 710 measured by the sensor 440 and images 720 acquired by the camera 450. Specifically, by using machine learning, the server 200 may estimate the degree of pollution of the cookware from the data 710 measured by the sensor 440 and the images 720 acquired by the camera 450. This may be a result of using the learning model stored in the model storage unit 231 of the server 200.

Specifically, a learning model generated by using the image of the cookware during the cooking operation, and/or a relationship between the amount of pollutant measured by the sensor and the degree of pollution of the cookware may be previously stored in the model storage unit 231 of the server 200. The server 200 may provide data received from the range hood 400 as input data by using the stored learning model and the artificial neural network 231a, and may receive the degree of pollution of the cookware used for the cooking operation, as output data 730.

The server 200 may create a recommended dish washing course to be used by the dishwasher, on the basis of the degree of pollution of the cookware. The recommended dish washing course 740 may include a type of washing cycle, washing time, and the amount of detergent. The server 200 may provide the dishwasher with a control command generated on the basis of the recommended dish washing course 740. The dishwasher may perform a dish washing operation according to the control command.

As described above, the integrated management system for the kitchen environment according to the embodiment of the present disclosure detects the change in the atmosphere environment of the kitchen through the camera attached to the range hood, and meanwhile, identifies the degree of pollution of the cookware and provides the dishwasher with the control command, thereby enhancing the user experience of the environment appliance and dish washing.

The present disclosure described above may be implemented as computer-readable code on a medium in which a program is recorded. A computer-readable medium includes all types of recording devices in which data readable by a computer system is stored. Examples of the computer-readable medium include a hard disk drive (HDD), a solid-state disk (SSD), a silicon disk drive (SDD), ROM, RAM, CD-ROM, a magnetic tape, a floppy disk, an optical data storage device, and the like. In addition, the computer may include the processor 180 of the terminal.

The embodiments of the present disclosure have been described above with reference to the accompanying drawings, but those skilled in the art will understand that the present disclosure may be implemented in other specific forms without changing the technical idea or essential characteristics of the present disclosure. Therefore, it should be understood that the embodiments described above are illustrative in all aspects and not restrictive.

What is claimed is:

1. An integrated management system for a kitchen environment using artificial intelligence, the system comprising:
    a range hood configured to be placed above a cooking appliance including a heater, the range hood including a sensor that measures information on an atmosphere environment changed due to an operation of the cooking appliance;
    a server configured to determine whether to execute a kitchen environment management mode, based on a result of measurement by the sensor; and
    multiple environment appliances registered in a user account and cooperating over a network, each of the multiple environment appliances receiving a control command corresponding to the kitchen environment management mode from the server, and operating according to the control command,
    wherein the range hood further includes a camera placed above the cooking appliance and acquiring an image of cookware with which cooking is performed and transmits the image of the cookware photographed by the camera to the server, and wherein the server estimates a degree of pollution of the cookware based on the image of the cookware and a variation of the atmosphere environment by using a pollution degree model of the cookware which is previously stored.

2. The system of claim 1, wherein the sensor detects at least one among gas, oil mist, and smoke discharged due to the operation of the cooking appliance.

3. The system of claim 2, wherein the range hood transmits a warning signal to the server when the at least one among the gas, the oil mist, and the smoke detected by the sensor is equal to or greater than a predetermined threshold value, and the server controls the cooking appliance so that output of the cooking appliance is decreased, when the warning signal is provided.

4. The system of claim 2, further comprising:

a user terminal displaying details of the control commands provided to the multiple environment appliances, wherein the server provides the user terminal with a warning message in a warning mode, and the user terminal outputs the warning message.

5. The system of claim 1, wherein the server detects a change in the information on the atmosphere environment by using a learning model in which the image of the cookware and the information on the atmosphere environment are previously stored.

6. The system of claim 1, wherein the multiple environment appliances include a dishwasher, and the server determines a washing cycle of the dishwasher, washing time, and an amount of detergent based on the estimated degree of pollution.

7. The system of claim 1, wherein the multiple environment appliances include an air purifier or an air conditioner, and the server generates, when the kitchen environment management mode is executed, the control command for increasing output of the air purifier or the air conditioner, and provides the control command to the air purifier or the air conditioner.

8. An integrated management method of a kitchen environment using artificial intelligence, the method comprising:

measuring, by a range hood placed above a cooking appliance including a heater, information on an atmosphere environment changed due to an operation of the cooking appliance, by using a sensor;

determining, by a server based on a result of measurement, whether to execute a kitchen environment management mode;

driving multiple environment appliances by using a control command corresponding to the kitchen environment management mode, wherein the multiple environment appliances are registered in a user account and cooperate over a network, wherein measuring information on an atmosphere environment changed due to an operation of the cooking appliance comprises acquiring, by a camera placed above the cooking appliance, an image of the cookware with which cooking is performed, and wherein determining whether to execute a kitchen environment management mode comprises estimating, by the server, a degree of pollution of the cookware based on the image of the cookware and a variation of the atmosphere environment by using a previously stored pollution degree model of the cookware.

9. The method of claim 8, wherein the sensor detects at least one among gas, oil mist, and smoke discharged due to the operation of the cooking appliance.

10. The method of claim 9, further comprising:

executing a warning mode when the at least one among the gas, the oil mist, and the smoke detected by the sensor is equal to or greater than a predetermined threshold value; and when the warning mode is executed, controlling the cooking appliance so that output of the cooking appliance is decreased.

11. The method of claim 10, further comprising:

providing, by the server, a user terminal with a warning message in the warning mode; and outputting, by the user terminal, the warning message.

12. The method of claim 8, wherein the determining, by the server, of whether to execute the kitchen environment management mode comprises:

detecting a change in the information on the atmosphere environment based on the image of the cookware and the information on the atmosphere environment by using a previously stored learning model.

13. The method of claim 8, wherein the multiple environment appliances include a dishwasher, and the server determines a washing cycle of the dishwasher, washing time, and an amount of detergent based on the estimated degree of pollution.

14. The method of claim 8, wherein the multiple environment appliances include an air purifier or an air conditioner, and the driving of the multiple environment appliances by using the control command corresponding to the kitchen environment management mode comprises:

generating the control command for increasing output of the air purifier or the air conditioner and providing the control command to air purifier or the air conditioner.

15. A non-transitory computer readable medium having instructions stored thereon for execution by a processor to perform:

measuring, by a range hood placed above a cooking appliance including a heater, information on an atmosphere environment changed due to an operation of the cooking appliance, by using a sensor;

determining, by a server based on a result of measurement, whether to execute a kitchen environment management mode;

driving multiple environment appliances by using a control command corresponding to the kitchen environment management mode, wherein the multiple environment appliances are registered in a user account and cooperate over a network, wherein measuring information on an atmosphere environment changed due to an operation of the cooking appliance comprises acquiring, by a camera placed above the cooking appliance, an image of the cookware with which cooking is performed, and wherein determining whether to execute a kitchen environment management mode comprises estimating, by the server, a degree of pollution of the cookware based on the image of the cookware and a variation of the atmosphere environment by using a previously stored pollution degree model of the cookware.

* * * * *